United States Patent
Liu et al.

(10) Patent No.: US 10,123,871 B2
(45) Date of Patent: Nov. 13, 2018

(54) IMPLANT CAPSULE AND IMPLANT DELIVERY SYSTEM

(71) Applicant: SHANGHAI MICROPORT CARDIOFLOW MEDTECH CO., LTD., Shanghai (CN)

(72) Inventors: Xiang Liu, Shanghai (CN); Baozhu Gui, Shanghai (CN); Yu Li, Shanghai (CN); Mingming Wu, Shanghai (CN); Zhixiu He, Shanghai (CN); Haishan Wang, Shanghai (CN)

(73) Assignee: Shanghai Microport Cardioflow Medtech Co., Ltd., Shanghai (CN)

( * ) Notice: Subject to any disclaimer, the term of this patent is extended or adjusted under 35 U.S.C. 154(b) by 99 days.

(21) Appl. No.: 15/036,902

(22) PCT Filed: Nov. 14, 2014

(86) PCT No.: PCT/CN2014/091091
§ 371 (c)(1),
(2) Date: May 16, 2016

(87) PCT Pub. No.: WO2015/070791
PCT Pub. Date: May 21, 2015

(65) Prior Publication Data
US 2016/0287385 A1    Oct. 6, 2016

(30) Foreign Application Priority Data

Nov. 18, 2013  (CN) .......................... 2013 1 0580969

(51) Int. Cl.
*A61F 2/962*    (2013.01)
*A61F 2/24*    (2006.01)
(Continued)

(52) U.S. Cl.
CPC .......... *A61F 2/2436* (2013.01); *A61F 2/2418* (2013.01); *A61F 2/962* (2013.01);
(Continued)

(58) Field of Classification Search
CPC .. A61F 2/95; A61F 2/962; A61F 2/966; A61F 2002/9586; A61M 25/005
See application file for complete search history.

(56) References Cited

U.S. PATENT DOCUMENTS 5,222,949 A * 6/1993 Kaldany ............... A61L 29/042
                                                    600/433
6,290,692 B1 * 9/2001 Klima ............... A61M 25/0052
                                                    604/264
(Continued)

FOREIGN PATENT DOCUMENTS

CN         101128168        2/2008
CN         101933821        1/2011
(Continued)

*Primary Examiner* — Diane Yabut
(74) *Attorney, Agent, or Firm* — Muncy, Geissler, Olds & Lowe, P.C.

(57) ABSTRACT

An implant capsule (10) and an implant delivery system are disclosed. The implant capsule (10) includes, sequentially from a proximal end to a distal end, a flexural section (102, 102a-102e), a reinforcement section (101, 101a-101e) and a radiopaque reinforcement ring (104a-104e). The reinforcement section (101, 101a-101e) has higher strength than the flexural section (102, 102a-102e). The implant delivery system includes the implant capsule (10). The implant capsule (10) can ensure the implant to be deployed in a coaxial condition and prevent over-expansion due to large expansion forces exerted by a stent of the implant.

8 Claims, 3 Drawing Sheets

(51) Int. Cl.
*A61M 25/00* (2006.01)
*A61F 2/958* (2013.01)
*A61F 2/966* (2013.01)

(52) U.S. Cl.
CPC ....... *A61F 2/966* (2013.01); *A61F 2002/9586* (2013.01); *A61M 25/005* (2013.01)

(56) References Cited

U.S. PATENT DOCUMENTS

| | | |
|---|---|---|
| 8,579,963 B2 | 11/2013 | Tabor |
| 2001/0034514 A1* | 10/2001 | Parker ................. A61M 25/005 604/525 |
| 2005/0004556 A1* | 1/2005 | Pursley ............. A61M 25/0012 604/529 |
| 2006/0089704 A1* | 4/2006 | Douglas .................... A61F 2/07 623/1.12 |
| 2007/0112355 A1 | 5/2007 | Salahieh et al. |
| 2008/0188928 A1 | 8/2008 | Salahieh et al. |
| 2009/0234443 A1 | 9/2009 | Ottma et al. |
| 2011/0251680 A1 | 10/2011 | Tran et al. |
| 2011/0251683 A1 | 10/2011 | Tabor |
| 2013/0123915 A1 | 5/2013 | Giannetti et al. |
| 2013/0226308 A1* | 8/2013 | Gerdts ..................... A61F 2/95 623/23.7 |
| 2013/0253343 A1* | 9/2013 | Waldhauser ......... A61B 5/0215 600/486 |
| 2013/0289697 A1* | 10/2013 | Baker .................... A61F 2/962 623/1.12 |

FOREIGN PATENT DOCUMENTS

| | | |
|---|---|---|
| CN | 101961269 | 2/2011 |
| CN | 102499801 | 6/2012 |
| CN | 102834072 | 12/2012 |
| CN | 103037808 | 4/2013 |
| CN | 203736348 | 7/2014 |
| JP | H 09140804 A | 6/1997 |
| JP | 2000-279529 A | 10/2000 |
| JP | 2010-527695 A | 8/2010 |
| JP | 2010-540176 A | 12/2010 |
| JP | 2012-513878 A | 6/2012 |
| JP | 2013-523327 A | 6/2013 |
| JP | 2013-539381 A | 10/2013 |
| WO | WO 2011/035327 A1 | 3/2011 |
| WO | WO 2014/189977 A1 | 11/2014 |

* cited by examiner

IMPLANT CAPSULE AND IMPLANT DELIVERY SYSTEM

TECHNICAL FIELD

The present invention relates to an implant capsule and an implant delivery system.

BACKGROUND

Heart valve diseases are some of the most commonly diagnosed cardiac diseases in China, and are mostly found to be heart valve damage caused by rheumatic fever. In recent years, the continually aging population has driven an increasing incidence of valvular degeneration (including calcification, mucoid degeneration, etc.) and valvular damage caused by metabolic disorders in China.

Conventionally, heart valve replacement surgery is an open-heart procedure conducted under general anesthesia, during which, following an incision made along the patient's sternum (sternotomy), the heart is stopped and blood flow is guided through a "heart-lung" bypass machine (extracorporeal circulation machine). Therefore, traditional open surgery brings to the patient significant trauma as well as possible transient disturbances caused by emboli and other issues associated with the use of the heart-lung machine Complete recovery from the trauma typically costs a couple of months. For some special population groups such as elders, the trauma is particularly unendurable and the recovery needs more time and is sometime even impossible.

Minimally invasive interventional surgery offers a variety of advantages, including needlessness of sternotomy, minimal patient trauma and quick recovery. In the recent ten years, the development shows that not only the diseases curable by traditional medical and surgical treatments but also some diseases that the traditional approaches could not handle can be treated by the interventional therapies. After entering the twenty-first century, researches on interventional therapies for valvular heart diseases have been experiencing a notable acceleration. Percutaneous valve implant techniques have evolved from experimental researches to small-scale clinical trials and are likely to have breakthroughs in technical "bottlenecks" to achieve extensive clinical applications. This makes the techniques again a focus of research efforts in the field of interventional cardiology.

The success of a minimally invasive procedure for implanting a prosthetic valve is critically dependent on how to deliver the prosthetic valve with a delivery system to a target site with ensured coaxial alignment between a sheath carrying the prosthesis and the original valvular lumen (annulus) until accurate positioning and deployment have been achieved.

U.S. patent Pub. No. US2011/0251683A1 describes a delivery system capable of loading or deploying a prosthetic heart valve by rotating or pushing/pulling operations. In addition, the system provides positioning and deployment functions, as well as a recapturing function when needed, by virtue of a design composed of an inner tube, a sheath and a stability tube. The sheath of the delivery system is homogenously a formed polymer tube, a braided polymer tube or a cut metal tube. During the recapturing process, the stability tube is advanced, increasing circumferential support of a prosthesis-retaining section of the sheath to the prosthesis and thereby effectuating the recapturing. The stability tube of the delivery system is a braided polymer tube. In addition, the Chinese patent document CN101961269A discloses a prosthetic valve delivery system including a sheath which is a polymer tube embedded with a metal braiding.

In the conventional delivery systems for use in interventional procedures, positioning accuracy is, however, not taken into account in the design of such sheaths homogenously as a formed polymer tube, a braided polymer tube or a metal tube for loading and retaining the prosthetic heart valve. Conventionally, in order to achieve the coaxial positioning, additional operating means for the delivery systems are sometimes utilized, as well as catheter steering mechanisms. However, additional difficulties in surgical operations are resulted from the directional requirements for advancement of the catheter of the delivery system in a vascular lumen, i.e., the catheter being required to so bend as to be adapted to the geometric profile of the vascular lumen.

Therefore, in the prior art, there are the following technical problems: 1) the design of the delivery systems does not take into account both the improving of positioning accuracy and prevention of the over-expansion of the sheath; and 2) positioning achieved by an additional steering function of the handle leads to increased difficulties in surgical operations.

SUMMARY OF THE INVENTION

It is an objective of the present invention to overcome at least one of the above problems in the prior art by developing an implant capsule and an implant delivery system, which can ensure the implant to be deployed in a coaxial condition and prevent over-expansion due to high expansion forces exerted by a stent of the implant.

Specifically, the present invention provides an implant capsule characterized in that the capsule includes, sequentially from a proximal end to a distal end, a flexural section, a reinforcement section and a radiopaque reinforcement ring, wherein the reinforcement section has higher strength than the flexural section.

Preferably, the reinforcement section is formed of a polymer material.

Preferably, the reinforcement section consists of a polymer tube and a reinforcement braiding disposed over the polymer tube.

Preferably, the reinforcement braiding is formed of metal filaments or polymer filaments having a coil pattern or a braided pattern.

Preferably, the reinforcement section is a metal tube provided with grooves formed by laser-cutting.

Preferably, the reinforcement section consists of a polymer tube and several reinforcement rings disposed over the polymer tube apart from one another, and the reinforcement rings are formed of a metal or polymer material having higher strength than the polymer tube.

Preferably, the flexural section is formed of a polymer material.

Preferably, the reinforcement section and the flexural section are integrally formed, or connected to each other at a connection point by means of hot melting or an adhesive.

Preferably, the reinforcement section and the flexural section, of the capsule, both have a smooth inner surface, or are both provided with an inner friction-reducing coating.

Preferably, the friction-reducing coating is made of polytetrafluoroethylene (PTFE) or polyethylene terephthalate (PET).

The present invention also provides an implant delivery system including, sequentially from a proximal end to a distal end, an operating handle and a catheter. The catheter includes a pushing tube, a capsule and an inner tube assembly. The capsule is in connection with the pushing tube. The inner tube assembly has a proximal end in fixed connection with the operating handle. The capsule and the pushing tube are disposed circumferentially over the inner tube assembly. The pushing tube is coupled to a control mechanism of the operating handle, under the control of which the pushing tube and the capsule are advanceable and retractable. The implant delivery system is characterized in that the capsule is the implant capsule as defined above.

In summary, the present invention provides an implant capsule with a structure that part of it is reinforced while the remainder of it is not, by means of, for example, adding a metal braiding or mutually-spaced reinforcement rings to a polymer tube base, or forming part of it with a metal tube. With this structure, coaxial alignment of the implant capsule and a valvular annulus can be achieved, which can facilitate implant positioning and deployment. At the same time, the implant capsule is strong enough to capsule the implant therein without being over-expanded due to large radial forces exerted by a stent of the implant.

Therefore, the implant capsule according to the present invention has the following advantages: 1) it reduces the risk of over-expansion due to high implant radial forces; 2) it ensures a desired coaxial alignment for implant deployment by a partially-reinforced structure which takes into account both constraining strength and bending capabilities.

BRIEF DESCRIPTION OF THE DRAWINGS

The accompanying drawings to be referenced in the following description of specific embodiments of the present invention are briefed below so that the subject-matter of the embodiments will become more apparent. It is apparent that the following drawings are merely the depictions of a few particular embodiments described herein and do not limit the scope of the invention in any way. It is a matter of course that those skilled in the art can make other embodiments and drawings without exerting inventive effort based on the disclosed embodiments and drawings.

DETAILED DESCRIPTION

In order for those skilled in the art to better understand the subject matter of the present application, a clear, complete description of the subject matter of embodiments of the invention is set forth below with reference to drawings pertaining thereto. Apparently, the described embodiments are a part of the embodiments of the invention rather than all of them. All other embodiments obtained by those of ordinary skill in the art based on the specific embodiments described below without exerting inventive effort are considered to fall within the scope of the present invention.

Figure 1:
FIG. 1 is a schematic illustration of an implant delivery system for minimally invasive intervention according to the present invention.

FIG. 1 is a schematic illustration of an implant delivery system for minimally invasive intervention according to the present invention. As illustrated in FIG. 1, the implant delivery system for minimally invasive intervention according to the present invention includes, sequentially from a distal end to a proximal end, a catheter 1 and an operating handle 2. The catheter 1 is connected to the operating handle 2.

Figure 2:
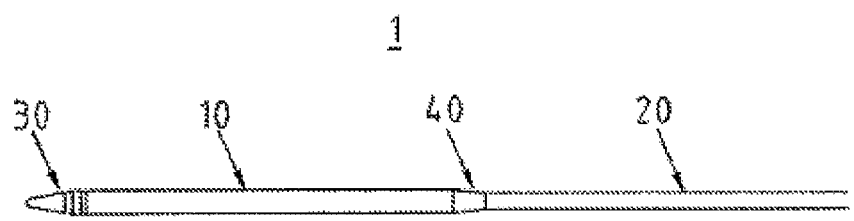
FIG. 2 is a schematic illustration of a catheter of the implant delivery system according to the present invention.

FIG. 2 is a schematic illustration of the catheter 1 of the implant delivery system according to the present invention. The catheter 1 of the implant delivery system according to the present invention is configured for the loading, positioning and deployment of an implant. As illustrated in FIG. 2, the catheter 1 of the implant delivery system according to the present invention includes a capsule 10, a pushing tube 20 and an inner tube assembly 30. The capsule 10 and the pushing tube 20 may be formed as an integral structure. As an alternative embodiment, the capsule 10 may be coupled to the pushing tube 20 at a connection point 40. The pushing tube 20 is coupled to the operating handle 2. Each of the capsule 10 and the pushing tube 20 is disposed circumferentially over the inner tube assembly 30, and defines a lumen having an inner diameter that is greater than an outer diameter of the inner tube assembly 30. An implant can be loaded within the capsule 10. The pushing tube 20 is connected to a control mechanism of the operating handle 2. The pushing tube 20 and the capsule 10 can be advanced and retracted under the control of the control mechanism.

Figure 3:
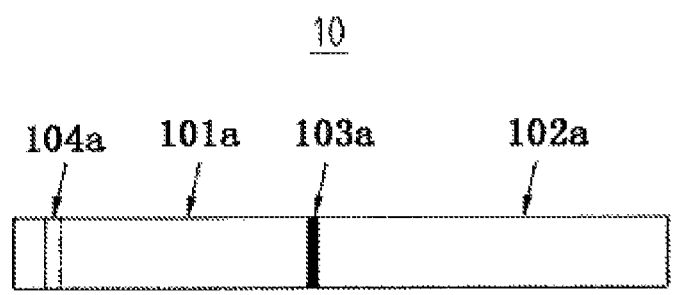
FIGS. 3 to 7 are schematics illustrating implant capsules of different structures according to the present invention.

FIG. 3 schematically shows an implant capsule 10 of a first structure according to the present invention. As shown in FIG. 3, the capsule 10 includes, sequentially from a proximal end to a distal end, a flexural section 102a, a reinforcement section 101a and a radiopaque reinforcement ring 104a. The reinforcement section 101a has higher strength than the flexural section 102a. The reinforcement section 101a serves primarily to constrain the implant. The flexural section 102a is provided mainly to ensure the capsule 10 to have desired flexibility in the process of implant positioning and deployment. In particular, the reinforcement section 101a is a tubular reinforcement member for constraining the higher radial force portion of the implant. That is, the higher radial force portion of the implant is disposed within the reinforcement section 101a. The flexural section 102a corresponds to a lower radial force portion of the implant. The flexural section 102a is so flexible that there is a desirable flexibility available during the positioning and deployment of the implant. That is, the lower radial force portion of the implant is disposed within the flexural section 102a. Those skilled in the art will readily understand that, in a state of being loaded in the capsule 10, the portion of the implant exerts high radial forces (herein, this portion is referred to as "higher radial force portion of the implant"), and the remaining portion thereof exerts low radial forces (herein, this portion is referred to as "lower radial force portion of the implant").

The reinforcement section 101a is formed of a polymer material having higher strength than the flexural section 102a. In this embodiment, the reinforcement section 101a may be integrally formed with the flexural section 102a as a single structure. As an alternative embodiment, the reinforcement section 101a may be connected to the flexural section 102a at a connection point 103a by means of, for example, hot melting or an adhesive. In this embodiment, the implant is a prosthetic heart valve.

Figure 4:
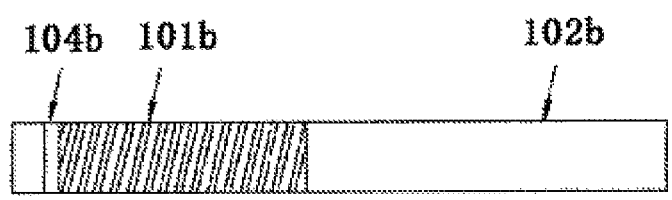

FIG. 4 shows an implant capsule of a second structure according to the present invention. The implant capsule of FIG. 4 is substantially the same as that of FIG. 3 in structure, and therefore only the differences therebetween are described below for simplicity of description. In the implant capsule shown in FIG. 4, the capsule 10 includes, sequentially from a proximal end to a distal end, a flexural section 102b, a reinforcement section 101b and a radiopaque reinforcement ring 104b. The reinforcement section 101b consists of a polymer tube and a reinforcement braiding which is disposed over the polymer tube and may have higher strength than the polymer tube. The reinforcement braiding may be formed of metal filaments or polymer filaments. In addition, the reinforcement braiding may have a coil pattern providing a reinforcement effect.

Figure 5:

FIG. 5 shows an implant capsule of a third structure according to the present invention. As the implant capsule of FIG. 5 is structurally similar to that of FIG. 3, only the differences therebetween are described below for brevity. In the implant capsule shown in FIG. 5, the capsule 10 includes, sequentially from a proximal end to a distal end, a flexural section 102c, a reinforcement section 101c and a radiopaque reinforcement ring 104c. The reinforcement section 101c consists of a polymer tube and a reinforcement braiding which is disposed over the polymer tube and may have higher strength than the polymer tube. The reinforcement braiding may be formed of metal filaments or polymer filaments. In addition, the reinforcement braiding may have a braided pattern also providing a reinforcement effect.

Figure 6:
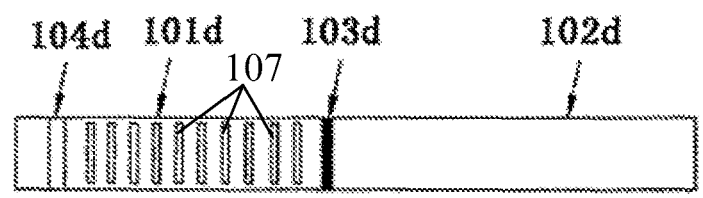

FIG. 6 shows an implant capsule of a fourth structure according to the present invention. As the implant capsule of FIG. 6 is structurally similar to that of FIG. 3, only the differences therebetween are described below for brevity. In the implant capsule shown in FIG. 6, the capsule 10 includes, sequentially from a proximal end to a distal end, a flexural section 102d, a reinforcement section 101d and a radiopaque reinforcement ring 104d. The reinforcement section 101d is a metal tube in which grooves 107 are formed by laser-cutting or the like such that the metal tube has a suitably increased flexibility and thus can more easily pass through an aortic arch 4. Each of the grooves 107 may extend at an angle perpendicular to a center axis of the capsule 10. The reinforcement section 101d and the flexural section 102d may be connected at a connection point 103d.

Figure 7:
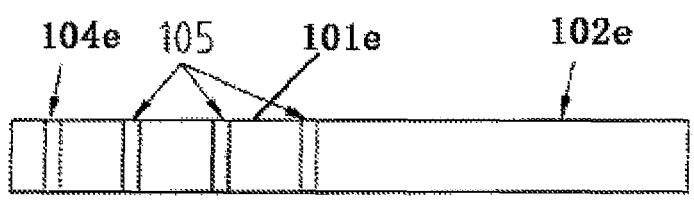

FIG. 7 shows an implant capsule of a fifth structure according to the present invention. As the implant capsule of FIG. 7 is structurally similar to that of FIG. 3, only its differences therefrom are described below for brevity. In the implant capsule shown in FIG. 7, the capsule 10 includes, sequentially from a proximal end to a distal end, a flexural section 102e, a reinforcement section 101e and a radiopaque reinforcement ring 104e. The reinforcement section 101e consists of a polymer tube and several reinforcement rings 105 which are disposed over the polymer tube apart from one another. The reinforcement rings 105 are metal or polymer rings having higher strength than the polymer tube. Each of the reinforcement rings extends in a direction perpendicular to a center axis of the capsule 10. The mutually spaced arrangement of the reinforcement rings 105 ensures good flexibility for the implant capsule.

In the embodiments of FIGS. 2 to 7, in order to ensure the capsule 10 to bend in a desired manner, the flexural sections 102a-102e each may be formed of a polymer material. As the flexural sections 102a-102e are each formed of a polymer material and correspond to the lower radial force portion of the implant being loaded, over-expansion of the capsule 10 will not occur. In addition, as the flexural sections 102a-102e are each formed of a homogenous polymer material, they are capable of geometrically adapted bending and can thus achieve desired coaxial alignment for implant positioning and deployment. Further, in each of the foregoing embodiments, the reinforcement section and the flexural section can be integrally formed, or the reinforcement section is connected to the flexural section at a connection point by means of hot melting or an adhesive.

In order to reduce the resistance to the implant during its delivery, the each lumen of the reinforcement sections 101a-101e and the flexural sections 102a-102e of the capsule 10 can be additionally provided with a friction-reducing inner coating. The friction-reducing inner coating may be, for example, a polytetrafluoroethylene (PTFE) layer, a polyethylene terephthalate (PET) layer or the like. In case of the capsule 10 provided with a connection point, the lumen of the connection point may also have such a friction-reducing inner coating. As an alternative embodiment, each of the reinforcement sections 101a-101e and the flexural sections 102a-102e of the capsule 10 may have the lumen with a smooth inner surface achievable by a mechanical process or selection of a suitable material.

Further, in FIGS. 1 to 7, the "proximal ends" correspond to the right-hand sides of the figures, i.e., the ends nearer to an operator. Likewise, the "distal ends" correspond to the left-hand sides of the respective figures, i.e., the ends farther from the operator.

Figure 8:
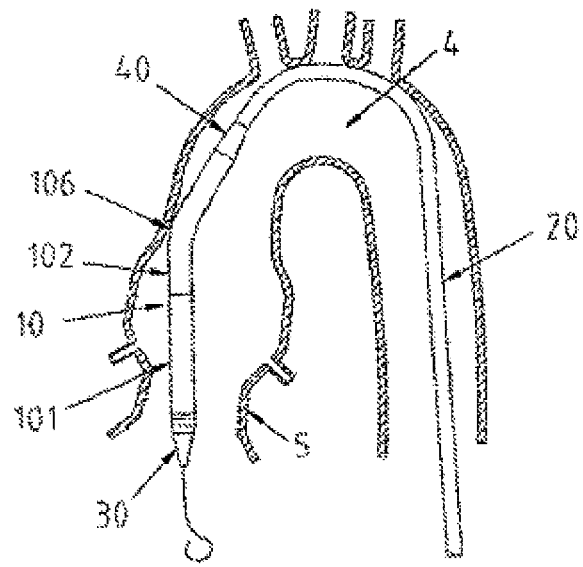
FIG. 8 is a schematic showing the delivery of an implant to a target site by the delivery system according to the present invention in which the implant is loaded.
Figure 9:
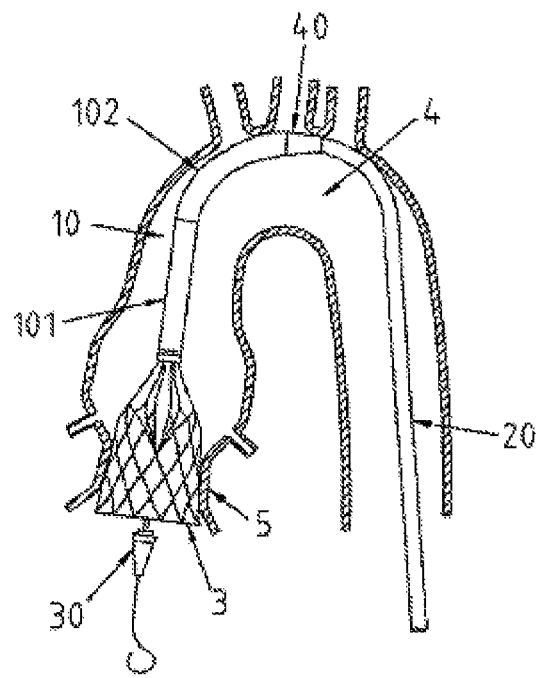
FIG. 9 is a schematic showing implant positioning and deployment effectuated by the delivery system according to the present invention in which the implant is loaded.

FIG. 8 is a schematic showing the delivery of an implant to a target site by a delivery system in which the implant is loaded, according to the present invention, and FIG. 9 is a schematic showing implant positioning and deployment effectuated by the delivery system in which the implant is loaded, according to the present invention. As shown in FIG. 8, the delivery system has a catheter including a capsule 10, a pushing tube 20 and an inner tube assembly 30. The capsule 10 is connected to the pushing tube 20 at a connection point 40. The capsule 10 includes a flexural section 102 and a reinforcement section 101. The self-expanding implant 3 (as showed in FIG. 9, an example of which is a prosthetic heart valve) is loaded in the capsule 10. When the catheter 1 passes through an aortic arch 4, the reinforcement section 101 reaches a valvular annulus 5. Because of the structure in which the portion of the self-expanding implant 3 corresponds to the flexural section 102 of the capsule 10 exerts lower radical forces, and since the corresponding portion of aortic has an arc-like profile, bending of the self-expanding implant 3 and the flexural section 102 occurs (at the point indicated at 106). Due to the bending point 106, the reinforcement section 101 is offset toward a center line of the valvular annulus 5, thereby leading to increased coaxial alignment.

As shown in FIG. 9, with an initial positioning being achieved, the operator can manipulate the operating handle 2 to retract the pushing tube 20 and hence the capsule 10 to be retracted, thereby slowly deploying the self-expanding implant 3. During the self-expansion of the self-expanding implant 3, the deployed portion of the self-expanding implant 3 will engage the valvular annulus 5. After accurate positioning has been achieved through simple adjustments, the self-expanding implant 3 is completed deployed by manipulations of the operator.

As the anchoring of the self-expanding implant 3 relies mainly on a portion thereof coming into contact with the valvular annulus 5, this portion of the self-expanding implant 3 is designed to exert high radial forces. This accordingly requires the reinforcement section 101 to have high radical constraining capabilities for preventing its over-expansion in diameter. As explained above, the reinforcement section 101 according to the present invention is just so designed to have the desirably increased strength which provides the radical constraining capabilities, thereby meeting the aforementioned requirements of surgical operations.

Further, since the flexural section 102 of the capsule 10, which corresponds to the lower radial force portion of the self-expanding implant 3 in a loaded condition, is selected to be formed of a polymer material, over-expansion of the capsule 10 can't happen. Furthermore, as the flexural section 102 is made of a homogenous polymer material and can hence bend in a desired way, the capsule 10 of the present invention can achieve the coaxial alignment needed for the positioning and deployment of the self-expanding implant 3.

In summary, the present invention provides an implant capsule with a structure that part of it is reinforced while the remainder of it is not, by means of, for example, adding a metal braiding or mutually-spaced reinforcement rings to a polymer tube base, or forming part of it with a metal tube. With this structure, coaxial alignment of the implant capsule and a valvular annulus can be achieved, which can facilitate implant positioning and deployment. At the same time, the implant capsule is strong enough to capsule the implant therein without being over-expanded due to large radial forces exerted by a stent of the implant.

Therefore, the inventive implant capsule has the following advantages: 1) it reduces the risk of over-expansion due to high implant radial forces; 2) it ensures a desired coaxial alignment for implant deployment by a partially-reinforced structure which takes into account both constraining strength and bending capabilities.

While the implant has been described as a prosthetic heart valve in the above embodiments, it will be appreciated by those skilled in the art that, apart from the prosthetic heart valve, the delivery system disclosed in the present invention can also be used to deliver an implant of any other type to a target site in the human body. That is, the delivery system according to the present invention is not limited to the delivery of a prosthetic heart valve but can also be used to deliver implants of different types.

The embodiments presented herein are described in a progressive manner emphasizing the differences of each embodiment from the other embodiments, and reference can be made between the embodiments for their same or similar features.

The embodiments described above are mere several particular embodiments of the present invention. It is noted that, for those skilled in the art, various combinations of the disclosed embodiments, as well as modifications and variations thereto, are possible without departing from the principles and concept of the present invention. It is intended that all such combinations, modifications and variations also fall within the scope of the present invention.

The invention claimed is:

1. A capsule for an implant, wherein the capsule comprises, sequentially from a proximal end to a distal end, a flexural section, a reinforcement section and a radiopaque reinforcement ring, wherein the reinforcement section has higher strength than the flexural section, wherein the reinforcement section consists of a polymer tube and a plurality of reinforcement rings disposed over the polymer tube apart from one another, wherein the plurality of reinforcement rings are formed of a metal or a polymer material having higher strength than the polymer tube, and wherein the plurality of reinforcement rings are individual and discrete rings.

2. The capsule of claim 1, wherein the flexural section is formed of a polymer material.

3. The capsule of claim 1, wherein
the reinforcement section is integrally formed with the flexural section.

4. The capsule of claim 1, wherein
the reinforcement section is connected to the flexural section at a connection point by means of hot melting or an adhesive.

5. The capsule of claim 1, wherein the reinforcement section and the flexural section, of the capsule, both have a smooth inner surface.

6. The capsule of claim 1, wherein the reinforcement section and the flexural section, of the capsule, are both provided with an inner friction-reducing coating.

7. The capsule of claim 6, wherein the friction-reducing coating is made of polytetrafluoroethylene or polyethylene terephthalate.

8. An implant delivery system comprising, sequentially from a proximal end to a distal end, an operating handle and a catheter, the catheter comprising a pushing tube, a capsule and an inner tube assembly, the capsule being in connection with the pushing tube, the inner tube assembly having a proximal end in fixed connection with the operating handle, the capsule and the pushing tube disposed circumferentially over the inner tube assembly, the pushing tube coupled to a control mechanism of the operating handle, wherein the pushing tube and the capsule are advanceable and retractable under control of the control mechanism, and wherein the capsule is a capsule as defined in claim 1.

* * * * *